(12) United States Patent
Onoue et al.

(10) Patent No.: US 12,396,987 B2
(45) Date of Patent: Aug. 26, 2025

(54) PHARMACEUTICAL COMPOSITION WITH EXCELLENT STORAGE STABILITY

(71) Applicants: ISHIHARA SANGYO KAISHA, LTD., Osaka (JP); SHIZUOKA PREFECTURAL UNIVERSITY CORPORATION, Shizuoka (JP)

(72) Inventors: Satomi Onoue, Shizuoka (JP); Hideyuki Sato, Shizuoka (JP); Takeshi Shindo, Osaka (JP)

(73) Assignees: ISHIHARA SANGYO KAISHA, LTD., Osaka (JP); SHIZUOKA PREFECTURAL UNIVERSITY CORPORATION, Shizuoka (JP)

( * ) Notice: Subject to any disclaimer, the term of this patent is extended or adjusted under 35 U.S.C. 154(b) by 371 days.

(21) Appl. No.: 16/976,270

(22) PCT Filed: Feb. 27, 2019

(86) PCT No.: PCT/JP2019/007425
§ 371 (c)(1),
(2) Date: Aug. 27, 2020

(87) PCT Pub. No.: WO2019/167979
PCT Pub. Date: Sep. 6, 2019

(65) Prior Publication Data
US 2021/0038576 A1 Feb. 11, 2021

(30) Foreign Application Priority Data
Mar. 1, 2018 (JP) ................. 2018-036837

(51) Int. Cl.
| | |
|---|---|
| A61K 31/44 | (2006.01) |
| A61K 47/02 | (2006.01) |
| A61K 47/18 | (2017.01) |
| A61K 47/22 | (2006.01) |
| A61K 47/40 | (2006.01) |

(52) U.S. Cl.
CPC ............. *A61K 31/44* (2013.01); *A61K 47/02* (2013.01); *A61K 47/183* (2013.01); *A61K 47/22* (2013.01); *A61K 47/40* (2013.01)

(58) Field of Classification Search
CPC .... A61K 9/0019; A61K 9/1652; A61K 47/10; A61K 47/22; A61K 9/08; A61K 9/2059; A61K 31/375; A61K 47/40; A61K 47/08; A61K 47/6951; A61K 2800/52
See application file for complete search history.

(56) References Cited

U.S. PATENT DOCUMENTS 6,653,333 B2 * 11/2003 Yotsuya ................. A61K 31/44
514/352

FOREIGN PATENT DOCUMENTS

| | | |
|---|---|---|
| CA | 3194011 A1 | 4/2022 |
| CN | 1058396 A | 2/1992 |
| CN | 1294511 A | 5/2001 |
| CN | 1400900 A | 3/2003 |
| CN | 101980605 A | 2/2011 |
| CN | 104546842 A | 4/2015 |
| EP | 0465913 A2 | 1/1992 |
| EP | 0465913 A3 | 4/1992 |
| JP | H06263735 A | 9/1994 |
| WO | 01/56568 A1 | 8/2001 |
| WO | 01/56569 A1 | 8/2001 |
| WO | 01/56570 A1 | 8/2001 |
| WO | 2010/137484 A1 | 12/2010 |
| WO | 2015080249 A1 | 6/2015 |

OTHER PUBLICATIONS

Strickley, R.G. "Solubilizing Excipients in Oral and Injectable Formulations." Feb. 2004. Pharmaceutical Research. 21(2): 201-230. (Year: 2004).*
Saline Enema Safety Data Sheet. May 2016. NATUREPLEX. (Year: 2016).*
Bharate et al., "Interactions and incompatibilities of pharmaceutical excipients with active pharmaceutial ingredients: a comprehensive review." Dec. 2010. J. Excipients and Food Chem. 1(3): 3-26. (Year: 2010).*
Irie, Cyclodextrins Toxic. and Safety Evaluation, p. 147 Feb. 1997.*
Loftson, Cyclodextrins Drug Sol. and Stabilization, Mar. p. 1017 (Year: 1996).*
May 21, 2019 (WO)—International Search Report PCT/JP2019/007425.
Sep. 1, 2020 (WO) International Preliminary Report on Patentability PCT/JP2019/007425.
Apr. 25, 2022 (MX) Office Action Application No. MX/A/2020/008992.
Nov. 12, 2021 (EP) Extended European Search Report Application No. 19761162.7.
Aug. 4, 2023 (JP) Office Action Application No. 2020-503545.
Nov. 3, 2022 (CN) Office Action Application No. 201980015622.2.
Mar. 3, 2023 (JP) Office Action Application No. 2020-503545.
Dec. 20, 2023 (AU) Office Action Application No. 2019228913.
Dec. 3, 2024 (CA) Office Action Application No. 3,092,616.
Apr. 23, 2025 (EP) Office Action Application No. 19761162.7.

* cited by examiner

*Primary Examiner* — Sarah Alawadi
*Assistant Examiner* — Thurman Wheeler
(74) *Attorney, Agent, or Firm* — Banner & Witcoff, Ltd.

(57) ABSTRACT

The present invention provides a composition which effectively enhances the stability of N-(2-ethylsulfonylamino-5-trifluoromethyl-3-pyridyl)cyclohexanecarboxamide or a salt thereof in a liquid composition. More specifically, the present invention provides a liquid composition comprising N-(2-ethylsulfonylamino-5-trifluoromethyl-3-pyridyl)cyclohexanecarboxamide or a salt thereof, a water-soluble additive and water.

7 Claims, 5 Drawing Sheets

PHARMACEUTICAL COMPOSITION WITH EXCELLENT STORAGE STABILITY

CROSS-REFERENCE TO RELATED APPLICATIONS

This application is based upon and claims the benefit of priority from Japanese Patent Application No. 2018-036837, filed on Mar. 1, 2018; the entire contents of which are incorporated herein by reference.

TECHNICAL FIELD

The present invention relates to a liquid composition comprising N-(2-ethylsulfonylamino-5-trifluoromethyl-3-pyridyl)cyclohexanecarboxamide or a salt thereof, with excellent stability.

BACKGROUND ART

It has been known that N-(2-ethylsulfonylamino-5-trifluoromethyl-3-pyridyl)cyclohexanecarboxamide or a salt thereof has an inhibitory effect on phospholipase A2 and is useful as an active ingredient of an anti-inflammatory agent or an anti-pancreatitis agent (Patent Document 1).

There has also been known a therapeutic agent or a prophylactic agent for gastrointestinal disease, liver disease, lung failure or shock containing N-(2-ethylsulfonylamino-5-trifluoromethyl-3-pyridyl)cyclohexanecarboxamide or a salt thereof as an active ingredient (Patent Documents 2, 3, 4 and 5).

Furthermore, the above Patent Documents 1 to 5 also mention a liquid composition such as a syrup suspension and a drug formulation composition such as an injection comprising the above active ingredient. However, when a liquid composition containing water was prepared in accordance with a method commonly used in this field, the stability of N-(2-ethylsulfonylamino-5-trifluoromethyl-3-pyridyl)cyclohexanecarboxamide or a salt thereof could not be said to be sufficient. Hence, it has been required to develop a technical means that can improve the stability of a liquid composition comprising N-(2-ethylsulfonylamino-5-trifluoromethyl-3-pyridyl)cyclohexanecarboxamide or a salt thereof.

PRIOR ART DOCUMENT

Patent Document

Patent Document 1
  JP H06-263735 A
Patent Document 2
  WO 2001/056568
Patent Document 3
  WO 2001/056569
Patent Document 4
  WO 2001/056570
Patent Document 5
  WO 2010/137484

SUMMARY OF THE INVENTION

This time, the present inventors have found that when a liquid composition comprising N-(2-ethylsulfonylamino-5-trifluoromethyl-3-pyridyl)cyclohexanecarboxamide or a salt thereof and water also contains a water-soluble additive, the stability of N-(2-ethylsulfonylamino-5-trifluoromethyl-3-pyridyl)cyclohexanecarboxamide or a salt thereof is improved.

N-(2-ethylsulfonylamino-5-trifluoromethyl-3-pyridyl)cyclohexanecarboxamide is represented by the structure formula of the following formula (1), and is hereinafter sometimes abbreviated as a compound of formula (1):

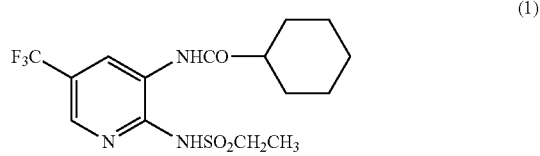

(1)

Therefore, an object of the present invention is to provide a liquid composition comprising N-(2-ethylsulfonylamino-5-trifluoromethyl-3-pyridyl)cyclohexanecarboxamide or a salt thereof and water, having enhanced stability of N-(2-ethylsulfonylamino-5-trifluoromethyl-3-pyridyl)cyclohexanecarboxamide or the salt thereof.

The present invention encompasses the following inventions:

[1] A liquid composition comprising
a compound of formula (1) or a salt thereof:

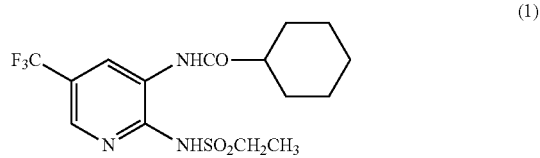

(1)

a water-soluble additive, and
water,
wherein, after storage at 40° C. for 2 weeks, a residual rate of the compound of formula (1) or a salt thereof in the composition is 90% or more by mass.

[2] The composition according to [1], wherein the water-soluble additive is at least one selected from the group consisting of a surfactant, cyclodextrin or a cyclodextrin derivative, and an antioxidant.

[3] The composition according to [2], wherein the surfactant is a nonionic surfactant.

[4] The composition according to [3], wherein the nonionic surfactant is selected from the group consisting of polyoxyethylene fatty acid ester, polyoxyethylene hydroxy fatty acid ester, poloxamer, polyoxyethylene castor oil, polyoxyethylene sorbitan fatty acid ester, polyoxyethylene hardened castor oil and a combination thereof.

[5] The composition according to any one of [2] to [4], wherein the cyclodextrin or the cyclodextrin derivative is selected from the group consisting of α-cyclodextrin, γ-cyclodextrin, hydroxypropyl-β-cyclodextrin, methyl-β-cyclodextrin, hydroxypropyl-α-cyclodextrin, hydroxypropyl-γ-cyclodextrin, sulfobutyl ether-β-cyclodextrin and a salt thereof, and a combination thereof.

[6] The composition according to any one of [2] to [5], wherein the antioxidant is selected from the group consisting of a radical scavenger, a singlet oxygen scavenger and a combination thereof.

[7] The composition according to [6], wherein the antioxidant is selected from the group consisting of vitamin C, cysteine, sodium sulfite, sodium azide and a combination thereof.

[8] The composition according to any one of [1] to [7], wherein the pH is 4 to 10.

[9] The composition according to any one of [1] to [8], wherein the content of the compound of formula (1) or a salt thereof in the composition is 0.01 to 1 w/v %.

[10] The composition according to any one of [1] to [9], wherein a mass ratio of the compound of formula (1) or a salt thereof to the water-soluble additive [compound of formula (1) or salt thereof:water-soluble additive] is 1:0.01 to 1:1,500.

[11] The composition according to any one of [1] to [10], wherein the composition is an aqueous solution, and the aqueous solution does not contain a precipitate after storage at 40° C. for 2 weeks.

[12] A product comprising the composition according to any one of [1] to [11] filled in a vial or a syringe.

[13] A decomposition inhibiting agent for a compound of formula (1) or a salt thereof comprising a water-soluble additive, wherein
the water-soluble additive is at least one selected from the group consisting of a surfactant, cyclodextrin or a cyclodextrin derivative, and an antioxidant.

[14] The agent according to [13], wherein a decomposition product from the compound of formula (1) or a salt thereof is at least one selected from compounds of formulas (2) to (4):

$$HOOC\underset{N}{\underset{|}{\diagdown}}\overset{NHCO-\diagup\diagdown}{\diagup}\diagdown NHSO_2CH_2CH_3 \quad (2)$$

$$ROC\underset{N}{\underset{|}{\diagdown}}\overset{NHCO-\diagup\diagdown}{\diagup}\diagdown NHSO_2CH_2CH_3 \quad (3)$$

$$F_3C\underset{N}{\underset{|}{\diagdown}}\overset{NH_2}{\diagup}\diagdown NHSO_2CH_2CH_3 \quad (4)$$

wherein R is an optionally substituted amino group or an optionally substituted alkoxy group.

[15] A method for inhibiting decomposition of a compound of formula (1) or a salt thereof, the method comprising making a water-soluble additive and the compound of formula (1) or a salt thereof coexist in a liquid composition containing water.

[16] A method for stabilizing a liquid composition, the method comprising making coexist a water-soluble additive, a compound of formula (1) or a salt thereof and water in the liquid composition.

According to the present invention, it is possible to effectively enhance the stability of the compound of formula (1) or a salt thereof in a liquid composition containing water. The stability preferably satisfies at least one of the following (i) and (ii): (i) after storage at 40° C. for 2 weeks, a residual rate of the compound of formula (1) or a salt thereof in the composition is 90% or more by mass, or (ii) the proportion of the peak area of a decomposition product derived from the compound of formula (1) to the total peak area by HPLC analysis of the composition obtained after storage at 40° C. for 2 weeks is 10% or less by area.

The composition of the present invention is advantageous for effectively enhancing the solubility of the compound of formula (1) or a salt thereof in the liquid composition containing water.

In the liquid composition of the present invention containing a water-soluble additive, the chemical stability of the compound of formula (1) or a salt thereof is improved, and the solubility of the compound of formula (1) or a salt thereof in water is also improved, making the composition have both chemical stability and physical stability, thus leading to improvement in usefulness particularly in practical use. More specifically, there can be provided a liquid composition and a product having practicality in which the compound of formula (1) or a salt thereof is not decomposed in the liquid composition for a long time (e.g., shelf life of the product), enabling maintenance of its effective amount, and the compound of formula (1) or a salt thereof does not precipitate in the liquid composition during storage.

DETAILED DESCRIPTION OF THE INVENTION

Figure 1:
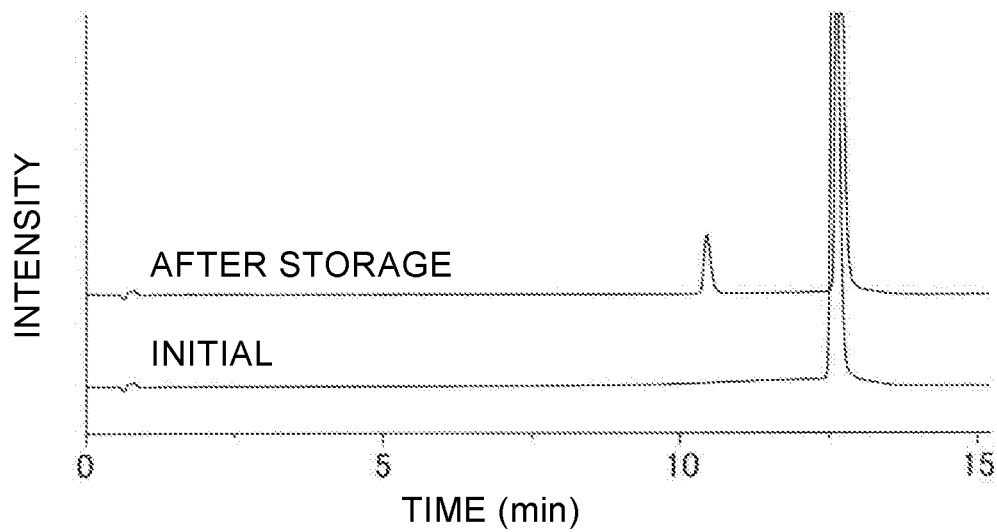
FIG. 1 is an HPLC chromatogram of an aqueous solution of N-(2-ethylsulfonylamino-5-trifluoromethyl-3-pyridyl)cyclohexanecarboxamide-monosodium salt-monohydrate (hereinafter also referred to as compound 1) before and after thermal decomposition.

One of the characteristics of a liquid composition of the present invention is to comprise a water-soluble additive together with N-(2-ethylsulfonylamino-5-trifluoromethyl-3-pyridyl)cyclohexanecarboxamide or a salt thereof and water.

N-(2-Ethylsulfonylamino-5-trifluoromethyl-3-pyridyl)cyclohexanecarboxamide or Salt Thereof N-(2-Ethylsulfonylamino-5-trifluoromethyl-3-pyridyl)cyclohexanecarboxamide in the present invention is represented by the structure formula of the above formula (1). A salt of the compound of formula (1) may be a pharmaceutically acceptable salt, and examples thereof include alkali metal salts such as a potassium salt and a sodium salt; alkaline earth metal salts such as a calcium salt; organic amine salts such as a triethanolamine salt, and a tris(hydroxymethyl)aminomethane salt, and the like. Furthermore, the salt of the compound of formula (1) may be one having water of crystallization among these salts, namely a hydrate.

The compound of formula (1) or a salt thereof can be produced, for example, by the method mentioned in JP H06-263735 A.

The content of the compound of formula (1) or a salt thereof in the composition of the present invention is not particularly limited as long as the effects of the present invention are not impaired, and examples thereof include 0.001 to 30 w/v (mass/volume) %, and it can be preferably 0.005 to 10 w/v %, and more preferably 0.01 to 1 w/v %, based on the whole composition.

Water-Soluble Additive

The water-soluble additive used in the present invention is not particularly limited, and includes ones that are used or that will be used in the future as drugs or foods.

The water-soluble additive of the present invention is not particularly limited as long as the effects of the present invention are exerted if it is an additive which is water-soluble. The term "water-soluble" of the water-soluble additive that can be used in the present invention is a nature belonging to the terms "very soluble", "freely soluble", "soluble" or "sparingly soluble" according to the General Notices of the Japanese Pharmacopoeia Seventeenth Edition. Regarding the water-soluble additive of the present invention, for example, the solubility in water is about 10 mg/mL or more, preferably about 33 mg/mL or more, more preferably 100 mg/mL or more, and still more preferably 1,000 mg/L or more at a usual handling temperature, for example, at a room temperature of near 20° C.

As the water-soluble additive in the present invention, a surfactant, cyclodextrin or a cyclodextrin derivative, or an antioxidant is preferable in terms of improvement in the stability of the compound 1 and/or improvement in the solubility in the liquid composition containing water.

Examples of the above surfactant include a nonionic surfactant, an anionic surfactant, a cationic surfactant, an amphoteric surfactant and a combination thereof, and the above surfactant is preferably a nonionic surfactant. Suitable examples of the above nonionic surfactant include a polyoxyethylene fatty acid ester, a polyoxyethylene hydroxy fatty acid ester, a poloxamer (polyoxyethylene-polyoxypropylene block copolymer), a polyoxyethylene castor oil, a polyoxyethylene sorbitan fatty acid ester, a polyoxyethylene hardened castor oil, polyethylene glycol and a combination thereof. Here, examples of the polyoxyethylene fatty acid ester include one in which fatty acid is C8 to C20 fatty acid and the average molar number of ethylene oxide added is 5 to 100, and more preferably polyoxyethylene monolaurate, polyoxyethylene monooleate and polyoxyethylene monostearate. Examples of the polyoxyethylene hydroxy fatty acid ester include one in which fatty acid is C8 to C20 fatty acid and the average molar number of ethylene oxide added is 5 to 100, and more preferably polyoxyethylene hydroxystearate, polyoxyethylene hydroxylaurate and polyoxyethylene hydroxyoleate. Examples of the poloxamer include one in which the average molar number of ethylene oxide or propylene oxide added is 10 to 200, and more preferably polyoxyethylene polyoxypropylene glycol such as polyoxyethylene (160) polyoxypropylene (30) glycol, polyoxyethylene (120) polyoxypropylene (40) glycol, polyoxyethylene (196) polyoxypropylene (67) glycol, polyoxyethylene (54) polyoxypropylene (39) glycol. Examples of the polyoxyethylene sorbitan fatty acid ester include one in which fatty acid is C8 to C20 fatty acid and the average molar number of ethylene oxide added is 5 to 100, and more preferably polyoxyethylene sorbitan oleate (e.g., polyoxyethylene (20) sorbitan oleate), polyoxyethylene sorbitan laurate and polyoxyethylene sorbitan stearate.

As the above nonionic surfactant, commercially available one may be used. Examples thereof include polyoxyethylene hydroxystearate such as trade name (the same hereinafter) Kolliphor (registered trademark) HS 15 (manufactured by BASF SE), a poloxamer such as Kolliphor (registered trademark) P188 (manufactured by BASF SE) and Kolliphor (registered trademark) P407, an polyoxyethylene castor oil such as Kolliphor (registered trademark) ELP (manufactured by BASF SE), polyoxyethylene sorbitan oleate such as Tween (registered trademark) 80 HP-LQ-(MH) (manufactured by CRODA) and Tween (registered trademark) 80 (manufactured by Wako Pure Chemical Industries, Ltd.) and an polyoxyethylene hardened castor oil such as NIKKOL (registered trademark) HCO-60 (manufactured by NIPPON SURFACTANT INDUSTRIES CO., LTD.).

In the present invention, use of the nonionic surfactant is advantageous for improving the solubility of the compound of formula (1) or a salt thereof in water. Use of the nonionic surfactant is also advantageous for imparting the chemical stability of the compound of formula (1) or a salt thereof. Imparting the stability is considered to be due to inhibition of hydrolysis of a trifluoromethyl group of the compound of formula (1) or a salt thereof.

Examples of the above cyclodextrin or cyclodextrin derivative include α-cyclodextrin, β-cyclodextrin, γ-cyclodextrin, an α-cyclodextrin derivative, a β-cyclodextrin derivative, a γ-cyclodextrin derivative and a salt thereof, and a combination thereof, and the above cyclodextrin or cyclodextrin derivative is preferably a cyclodextrin derivative. Examples of the salt of the cyclodextrin or the cyclodextrin derivative include a sodium salt, a potassium salt and the like. Examples of the cyclodextrin derivative include methylated, hydroxypropylated, sulfobutyl etherified, and/or acetylated α-cyclodextrin, β-cyclodextrin, γ-cyclodextrin and a combination thereof. Preferred examples of the cyclodextrin derivative include hydroxypropyl-β-cyclodextrin, methyl-β-cyclodextrin, dimethyl-β-cyclodextrin, sulfobutyl ether-β-cyclodextrin, hydroxypropyl-α-cyclodextrin, hydroxypropyl-γ-cyclodextrin and a combination thereof.

As the above cyclodextrin or cyclodextrin derivative, commercially available one may be used. Examples thereof include hydroxypropyl-β-cyclodextrin such as trade name Celldex (registered trademark) HP-β-CD (manufactured by NIHON SHOKUHIN KAKO CO., LTD.), methyl-β-cyclodextrin (manufactured by JUNSEI CHEMICAL CO., LTD.), 2-hydroxypropyl-α-cyclodextrin (manufactured by Aldrich) and sulfobutyl ether-β-cyclodextrin (NACALAI TESQUE, INC.).

In the present invention, use of the cyclodextrin or the cyclodextrin derivative is advantageous for imparting the chemical stability of the compound of formula (1) or a salt thereof. Imparting the stability is considered to be due to inhibition of hydrolysis of a trifluoromethyl group of the compound of formula (1) or a salt thereof. Use of the cyclodextrin or the cyclodextrin derivative is advantageous for not adversely affecting the blood kinetics of the compound of formula (1) or a salt thereof. Without being bound by any theory, it is believed that inclusion of at least a part of the compound of formula (1) or a salt thereof, for example, a trifluoromethyl group, in the cyclodextrin or the cyclodextrin derivative contributes to imparting the chemical stability and avoiding adverse effects on blood kinetics as mentioned above. Use of the cyclodextrin or the cyclodextrin derivative is preferable for improving the solubility of the compound of formula (1) or a salt thereof in water.

Examples of the above antioxidant include a radical scavenger, a singlet oxygen scavenger and a combination thereof, and the above antioxidant is preferably a radical scavenger and a singlet oxygen scavenger. Specific examples of the radical scavenger include vitamin C, cysteine, mannitol, vitamin E and a salt thereof, and a combination thereof, and the radical scavenger is preferably vitamin C. Examples of the singlet oxygen scavenger include sodium sulfite, sodium azide and a combination thereof, and the singlet oxygen scavenger is preferably sodium sulfite.

As the above antioxidant, commercially available one may be used. Examples thereof include L-ascorbic acid (NACALAI TESQUE, INC.), cysteine such as L-cysteine (manufactured by Aldrich), sodium azide ($NaN_3$) (Wako Pure Chemical Industries, Ltd.) and sodium sulfite ($Na_2SO_3$) (Wako Pure Chemical Industries, Ltd.).

In the present invention, use of a specific antioxidant is advantageous for imparting the chemical stability of the compound of formula (1) or a salt thereof. Imparting the stability is considered to be due to inhibition of hydrolysis of a trifluoromethyl group of the compound of formula (1) or a salt thereof. Use of a specific antioxidant is advantageous for not adversely affecting the blood kinetics of the compound of formula (1) or a salt thereof.

As the above-mentioned water-soluble additive, for example, a surfactant, cyclodextrin or a cyclodextrin derivative and an antioxidant may be used in combination, and examples of the combination include a combination of a surfactant and cyclodextrin or a cyclodextrin derivative, a combination of a surfactant and an antioxidant, a combination of cyclodextrin or a cyclodextrin derivative and an antioxidant, and a combination of a surfactant, cyclodextrin or a cyclodextrin derivative and an antioxidant. Here, examples of a preferred surfactant in the above combination include a polyoxyethylene hydroxy fatty acid ester, a poloxamer and a polyoxyethylene sorbitan fatty acid ester, examples of preferred cyclodextrin or cyclodextrin derivative include hydroxypropyl-β-cyclodextrin, examples of a preferred antioxidant include vitamin C, cysteine and sodium azide ($NaN_3$), and examples of a more preferred antioxidant include vitamin C and cysteine. Specific examples thereof include a combination of a polyoxyethylene hydroxy fatty acid ester and hydroxypropyl-β-cyclodextrin, a combination of a poloxamer and hydroxypropyl-β-cyclodextrin, a combination of a polyoxyethylene hydroxy fatty acid ester and vitamin C, a combination of a poloxamer and vitamin C, a combination of a polyoxyethylene hydroxy fatty acid ester, hydroxypropyl-β-cyclodextrin and vitamin C, a combination of a poloxamer, hydroxypropyl-β-cyclodextrin and vitamin C, a combination of a polyoxyethylene sorbitan fatty acid ester and vitamin C, a combination of a polyoxyethylene sorbitan fatty acid ester and cysteine, and a combination of a polyoxyethylene sorbitan fatty acid ester and sodium azide.

The content of the water-soluble additive in the composition of the present invention is not particularly limited as long as the effects of the present invention are not impaired, and examples thereof include 0.0001 to 70 w/v %, preferably 0.001 to 60 w/v %, and more preferably 0.5 to 50 w/v %, based on the whole composition.

Here, when two or more water-soluble additives are used, the content of the water-soluble additive mentioned above may be the total amount of these water-soluble additives.

The content of the surfactant in the composition of the present invention is not particularly limited as long as the effects of the present invention are not impaired, and examples thereof include 0.0001 to 70 w/v %, preferably 0.001 to 60 w/v %, and more preferably 0.5 to 30 w/v %, based on the whole composition.

The content of the cyclodextrin or the cyclodextrin derivative in the composition of the present invention is not particularly limited as long as the effects of the present invention are not impaired, and examples thereof include 0.0001 to 70 w/v %, preferably 0.001 to 60 w/v %, and more preferably 1 to 50 w/v %, based on the whole composition.

The content of the antioxidant in the composition of the present invention is not particularly limited as long as the effects of the present invention are not impaired, and examples thereof include 0.0001 to 70 w/v %, preferably 0.001 to 30 w/v %, and more preferably 0.01 to 20 w/v %, based on the whole composition.

In the composition of the present invention, a mass ratio of the compound of formula (1) or a salt thereof to the water-soluble additive [mass ratio of compound of formula (1) or salt thereof:water-soluble additive] is preferably 1:0.01 to 1:1,500, more preferably 1:0.01 to 1:1,400, and still more preferably 1:0.02 to 1:1,300. Here, when two or more water-soluble additives are used, the mass of the water-soluble additive mentioned above may be the total of these water-soluble additives.

Moreover, as shown in Examples mentioned later, the composition of the present invention can remarkably improve the sustained-release ability of the compound of formula (1) or a salt thereof. Therefore, according to another preferred embodiment of the present invention, the composition of the present invention is provided as a sustained-release composition of the compound of formula (1) or a salt thereof. Examples of a water-soluble additive in the sustained-release composition include a surfactant, and the water-soluble additive is preferably a nonionic surfactant, and more preferably a poloxamer, in terms of improvement in the sustained release. Furthermore, the content of the water-soluble additive in the composition of the present invention is preferably 20 to 40% by mass in terms of sustained release. Furthermore, a mass ratio of the compound of formula (1) or a salt thereof to the water-soluble additive in the composition of the present invention is preferably 1:10 to 1:200 in terms of sustained release.

Water

The water used in the present invention is not particularly limited, and includes one that is used or that will be used in the future as drugs or foods. Examples thereof include purified water, ion exchange water, distilled water, ultrafiltered water, ultrapure water (e.g., Milli-Q water), water for injection, physiological saline and the like.

Composition

The composition of the present invention can effectively improve the stability of the compound of formula (1) or a salt thereof of the present invention in a liquid composition. Specific examples of the improvement in the stability include the fact that, (i) after storage at 40° C. for 2 weeks, a residual rate of the compound of formula (1) or a salt thereof in the composition is 90% or more by mass, preferably 92% or more by mass, and more preferably 94% or more by mass. The conditions in which the compounds of formula (1), formula (2), formula (3) and formula (4) can be separated are performed under the following measurement conditions:

TABLE 1

| Column temperature | 20 to 50° C. |
|---|---|
| Mobile phase | Water/acetonitrile = 10/90 to 90/10 (containing 0.1 to 1% of acetic acid) |
| Flow rate | 0.3 to 1.5 mL/min |
| Detection | 276 nm |
| Column | C18 reverse-phase HPLC column |
| Detector | Ultraviolet detector |

Specific measurement conditions of HPLC mentioned above should be adjusted so that the same test results as in Example 1 mentioned later are obtained. More specifically, the conditions are adjusted so that the retention time of each compound to be measured is in the same range as the retention time mentioned in Example 1. Therefore, preferred measurement conditions mentioned above are according to Example 1. The residual rate is calculated by calculating the content of the compound of formula (1) or a salt thereof in the composition before and after storage at 40° C. for 2 weeks using a calibration curve, and by dividing the content after storage by the content before storage (e.g., initial content).

The improvement in the stability of the composition of the present invention may be improvement in inhibition of decomposition of the compound of formula (1) or a salt thereof. Examples of a decomposition product produced when the compound of formula (1) is decomposed include compounds of the following formulas (2) to (4) (compounds of formulas (2) and (4) are hereinafter also referred to as decomposition products D1 and D3, respectively):

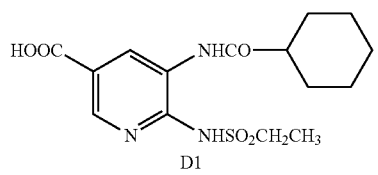
(2)

D1

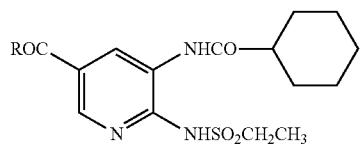
(3)

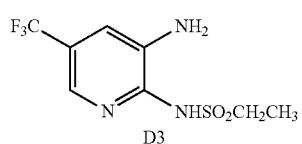
(4)

D3 wherein R is an optionally substituted amino group or an optionally substituted alkoxy group.

The optionally substituted amino group or optionally substituted alkoxy group in formula (3) mentioned above is not particularly limited as long as it is a group derived from amino acid, alcohols and/or amines which is generally used in the pharmaceutical field and a group derived from the water-soluble additive of the present invention. Examples of the amino acid include glycine, alanine, valine, leucine, isoleucine, serine, threonine, cysteine, methionine, asparagine, aspartic acid, glutamine, glutamic acid, proline, phenylalanine, tyrosine and tryptophan. Examples of the alcohols and/or amines include sugar alcohols such as xylitol, sorbitol, maltitol, maltotriose, mannitol, sucrose, erythritol, glucose, fructose, maltose and xylitose; monohydric alcohols such as methanol, ethanol, n-propyl alcohol, isopropyl alcohol and n-butyl alcohol; dihydric alcohols such as ethylene glycol, propylene glycol, dipropylene glycol, trimethylene glycol, 1,2-butylene glycol and 1,3-butylene glycol; glycerin, glycofurol, benzyl alcohol and the following compounds:

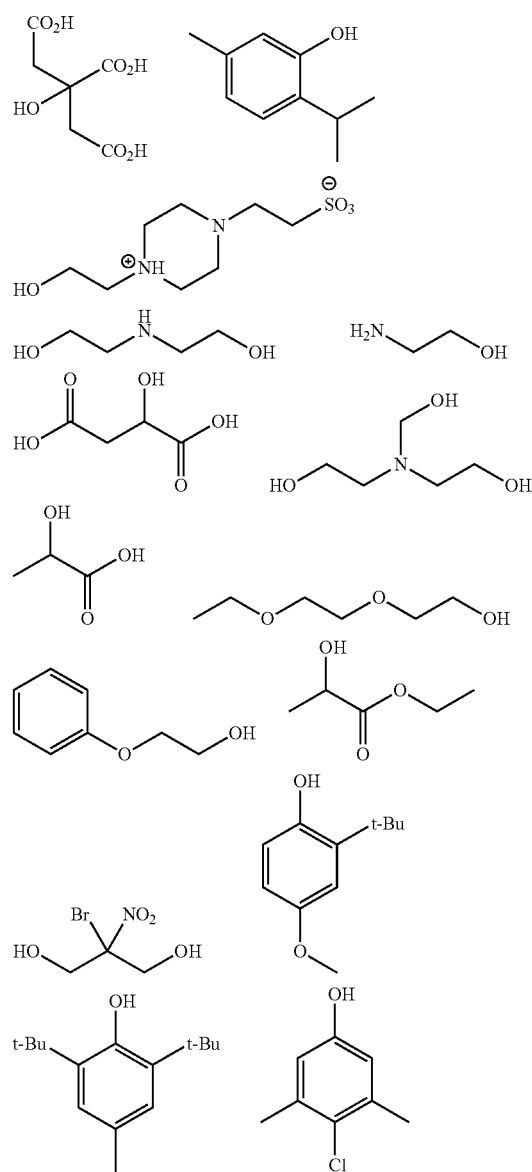

-continued

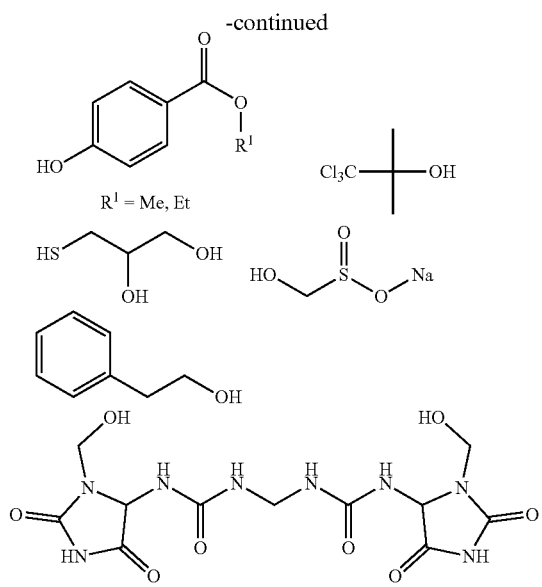

As mentioned above, the improvement in the stability of the composition of the present invention may be improvement in inhibition of decomposition of the compound of formula (1) or a salt thereof. Therefore, according to the composition of the present invention, examples of the improvement in the stability include the fact that (ii) the proportion of the peak area of a decomposition product derived from the compound of formula (1) to the total peak area by HPLC analysis of the composition obtained after storage at 40° C. for 2 weeks is 10% or less by area, preferably 8% or less by area, and more preferably 6% or less by area. Here, the above HPLC analysis can be performed under the same measurement conditions as for the above-mentioned (i) residual rate of the compound of formula (1) or a salt thereof in the composition after storage at 40° C. for 2 weeks. The proportion of the peak area of a decomposition product derived from the compound of formula (1) can be calculated using the area percentage method.

Furthermore, according to another embodiment of the present invention, there is provided a liquid composition comprising the compound of formula (1) or a salt thereof, a water-soluble additive and water, which satisfies at least one of the following (i) and (ii): (i) the content of the compound of formula (1) or a salt thereof in the composition is 0.001 to 30 w/v %, preferably 0.005 to 10 w/v %, and more preferably 0.01 to 1 w/v %, (ii) the proportion of the peak area of a decomposition product derived from the compound of formula (1) to the total peak area by HPLC analysis of the composition is 10% or less by area, preferably 8% or less by area, and more preferably 6% or less by area.

Furthermore, the composition of the present invention contains a pharmaceutically or orally acceptable additive as needed, and examples thereof include, but are not particularly limited to, aqueous vehicles, solvents, bases, solubilizing agents, isotonizing agents, stabilizers, preservatives, antiseptics, adjusters, chelating agents, pH adjusters, buffers, excipients, thickeners, coloring agents, aromatics, flavors, antioxidants, dispersants, disintegrants, plasticizers, emulsifiers, solubilizers, reducing agents, sweetening agents, corrigents, binders and the like. The additive can be mixed insofar as the effects of the present invention are not impaired. Here, the pharmaceutically or orally acceptable additive may be an embodiment in which a buffer is dissolved in water, and examples thereof include a phosphate buffer and a Britton-Robinson buffer.

A form of the composition of the present invention is preferably a liquid. Here, the liquid composition of the present invention may be a liquid immediately after preparation, at the time of administration or at a specific temperature (e.g., room temperature). Therefore, the liquid composition of the present invention, for example, may be a hydrogel by cooling, etc., at the time of administration, or may be a hydrogel in situ such as in vivo after administration, and the liquid composition of the present invention also encompasses the embodiment (hereinafter also referred to as hydrogelated liquid composition). The composition of the present invention includes a combination of the compound of formula (1) or a salt thereof, a water-soluble additive and water, but the dosage form is not particularly limited as long as the characteristics of the combination are maintained, and it can be provided as an injection such as an implantable injection and a long-acting injection, an drop, an eye drop, a nasal drop, an ear drop, a lotion, a syrup, an enema agent and the like. The above dosage form is preferably an injection. Here, examples of the injection include a product comprising the composition of the present invention filled in a vial or a syringe.

When the composition of the present invention is an aqueous solution, the aqueous solution preferably does not contain a precipitate after storage at 40° C. for 2 weeks. Here, the term "does not contain a precipitate" means that any precipitate in which the composition can be seen by a human eye is not confirmed by the method in Example 1 mentioned later.

The pH of the composition of the present invention is not particularly limited as long as the effects of the present invention are not impaired, and examples thereof include 4 to 10, and in order to improve the solubility, the pH is preferably 5 to 10, and more preferably 6 to 10. The pH of the composition of the present invention is preferably 4 to 9, and more preferably 4 to 8 in terms of improvement in the stability. The pH of the composition of the present invention is preferably 4 to 9, more preferably 5 to 8, and still more preferably 6 to 8. The measurement time point of the pH of the composition of the present invention is not particularly limited, and the initial pH of the composition produced and/or the pH of the composition after storage at 40° C. for 2 weeks is/are preferred.

The composition of the present invention is not particularly limited as long as the effects of the present invention are not impaired, and it can be systemically or locally administered. Specific administration includes drip infusion, injection such as intravenous injection, intramuscular injection, subcutaneous injection and intradermal injection, oral administration, transmucosal administration, transdermal administration, intranasal administration, intraoral administration and the like, and the administration is preferably injection, and more preferably intravenous injection and subcutaneous injection.

When the liquid composition of the present invention is a hydrogelated liquid composition, topical administration of the above composition can effectively deliver the compound of formula (1) or a salt thereof into the body.

Here, topical administration of the present invention refers to an administration form in which the compound of formula (1) or a salt thereof is retained locally (at an administration site) to be absorbed in the body. The composition of the present invention can be suitably used for not only a local action but also a systemic action.

Examples of the topical administration include parenteral administration, such as intramuscular administration, subcutaneous administration, intradermal administration, transmucosal administration such as transrectal administration, transdermal administration, intranasal administration, intraoral administration, intraperitoneal administration, intraarticular administration, intraocular administration, intratumoral administration, perivascular administration, intracranial administration, periocular administration, intrapalpebral administration, intravesical administration, intravaginal administration, intraurethral administration, intrarectal administration, adventitial administration, transnasal administration and the like. According to a preferred embodiment of the present invention, the composition of the present invention is provided as a composition for subcutaneous administration.

The composition of the present invention can be produced by a known method such as mixing the compound of formula (1) or a salt thereof and a water-soluble additive with water together with other solvents, etc., as needed. For example, the composition of the present invention can be produced by a known method such as mixing the compound of formula (1) or a salt thereof and a water-soluble additive with water and/or other solvents, etc., to dissolve, and more specific examples thereof include methods such as (A) mixing the compound of formula (1) or a salt thereof with a water-soluble additive, followed by addition of water, (B) mixing water with a water-soluble additive, followed by addition of the compound of formula (1) or a salt thereof, and (C) mixing water with the compound of formula (1) or a salt thereof, followed by addition of a water-soluble additive. In the production of the composition of the present invention, homogenization treatment or sterilization treatment may be performed to the above mixture, etc., as long as the effects of the present invention are not impaired.

The other solvents used for preparation of the above mixture are not particularly limited, and include ones that are used or that will be used in the future as drugs or foods. Specific examples of the above other solvents include alcohols (e.g., methanol, ethanol, propanol, propylene glycol, etc.), organic acids (e.g., acetic acid, propionic acid, etc.), polyethylene glycol or a mixed solvent thereof.

The composition of the present invention can be widely applied to a disease, a pathological condition or a symptom associated with an inflammatory cell (e.g., granulocytes (neutrophils, eosinophils, basophils), lymphocytes (e.g., T-lymphocytes, NK cells), monocytes, macrophages, plasma cells, mast cells, platelets) (e.g., pancreatitis, operative stress, disseminated intravascular coagulation (DIC), neoplastic disease, pyometra, heat stroke, immune-mediated hemolytic anemia (IMHA), sepsis, angiosarcoma, gastric volvulus, ischemia-reperfusion injury, purpura, liver failure, hepatitis, pneumonia, systemic inflammatory response syndrome (SIRS), trauma, osteoarthritis, cystitis, disk disease, atopy/allergy, dermatitis, immune-mediated disease, otitis, inflammatory bowel disease, chronic pain, colitis, chronic obstructive pulmonary disease (COPD), cholecystitis, cholangitis, etc.). Advantageously, the composition of the present invention can exert treatment and preventive effects on pancreatitis, operative stress, disseminated intravascular coagulation (DIC) and the like. Therefore, according to another embodiment of the present invention, the composition of the present invention is provided as a composition for treatment or prevention of a disease, a pathological condition or a symptom associated with an inflammatory cell, preferably pancreatitis, operative stress or disseminated intravascular coagulation (DIC). The composition of the present invention can also be used as a drug and a quasi drug for humans or animals. The composition of the present invention may be appropriately used in combination with other drugs and quasi drugs that are regularly used in this technical field, as needed.

According to one embodiment, examples of a subject to which the composition of the present invention is applied include animals, and the subject is preferably non-human animals such as mammals, birds, reptiles, amphibians and fishes, and more preferably mice, rats, rabbits, dogs, cats, pigs, cattle and horses. The above animal may be livestock, pets, domestic animals, wild animals and racing animals. The above subject may be healthy individuals (healthy animals) or may be patients (patient animals).

According to another embodiment of the present invention, there is provided a method for treating or preventing a disease a pathological condition or a symptom associated with an inflammatory cell of a subject, preferably pancreatitis, operative stress or disseminated intravascular coagulation (DIC), comprising administration of the composition of the present invention comprising an effective amount of the compound of formula (1) or a salt thereof to the subject. According to further another embodiment of the present invention, the above-mentioned method for preventing a disease, a pathological condition or a symptom associated with an inflammatory cell of a subject is regarded as a non-therapeutic method excluding medical practice when the subject is a healthy individual. The method for treating or preventing a disease, a pathological condition or a symptom, etc., associated with an inflammatory cell of a subject of the present invention can be performed in accordance with the contents mentioned herein for the composition of the present invention.

The effective amount of the compound of formula (1) or a salt thereof of the present invention and the frequency of administration of the composition of the present invention are not particularly limited, and are appropriately determined by a person skilled in the art depending on the type and purity of the compound of formula (1) or a salt thereof, the dosage form of the composition, and the type, nature, sex, age, symptoms, etc., of the subject. For example, the effective amount of the compound of formula (1) or a salt thereof is 0.01 to 1,000 mg/body weight kg, and preferably 0.05 to 500 mg/body weight kg. The frequency of administration is, for example, once to five times per day, preferably once to three times per day, and more preferably once to twice per day. The administration period is, for example, 1 to 7 days, preferably 1 to 5 days, and more preferably 1 to 3 days.

According to another embodiment of the present invention, there is provided use of a combination of the compound of formula (1) or a salt thereof, a water-soluble additive and water in the production of a liquid composition, wherein the liquid composition satisfies at least one of the following (i) and (ii): (i) after storage at 40° C. for 2 weeks, a residual rate of the compound of formula (1) or a salt thereof in the composition is 90% or more by mass, or (ii) the proportion of the peak area of a decomposition product derived from the compound of formula (1) to the total peak area by HPLC analysis of the composition obtained after storage at 40° C. for 2 weeks is 10% or less by area. According to another preferred embodiment of the present invention, the above composition is used for treatment or prevention of a disease, a pathological condition or a symptom associated with an inflammatory cell, preferably pancreatitis, operative stress or disseminated intravascular coagulation (DIC).

According to another embodiment of the present invention, there is provided a decomposition inhibiting agent of the compound of formula (1) or a salt thereof comprising a water-soluble additive, wherein the water-soluble additive is at least one selected from the group consisting of a surfactant, cyclodextrin or a cyclodextrin derivative, and an antioxidant. Here, examples of the decomposition product derived from the compound of formula (1) or a salt thereof include at least one selected from compounds of formulas (2) to (4). According to one embodiment of the present invention, there is provided use of at least one water-soluble additive selected from the group consisting of a surfactant, cyclodextrin or a cyclodextrin derivative, and an antioxidant in the production of the decomposition inhibiting agent of the compound of formula (1) or a salt thereof. According to one embodiment of the present invention, there is provided use of at least one water-soluble additive selected from the group consisting of a surfactant, cyclodextrin or a cyclodextrin derivative, and an antioxidant for inhibition of decomposition of the compound of formula (1) or a salt thereof. According to one embodiment of the present invention, there is provided at least one water-soluble additive selected from the group consisting of a surfactant, cyclodextrin or a cyclodextrin derivative, and an antioxidant for inhibition of decomposition of the compound of formula (1) or a salt thereof. In the above embodiment, the above inhibition of decomposition preferably satisfies at least one of the following (i) and (ii) when a decomposition inhibiting agent and the compound of formula (1) or a salt thereof is made coexist in a liquid composition containing water: (i) after storage at 40° C. for 2 weeks, a residual rate of the compound of formula (1) or a salt thereof in the composition is 90% or more by mass, or (ii) the proportion of the peak area of a decomposition product derived from the compound of formula (1) to the total peak area by HPLC analysis of the composition obtained after storage at 40° C. for 2 weeks is 10% or less by area.

According to another embodiment of the present invention, there is provided a method for inhibiting decomposition of the compound of formula (1) or a salt thereof, the method comprising making a water-soluble additive and the compound of formula (1) or a salt thereof coexist in a liquid composition containing water. According to one embodiment of the present invention, there is provided a method for inhibiting decomposition of the compound of formula (1) or a salt thereof, the method comprising making a water-soluble additive and the compound of formula (1) or a salt thereof coexist in a liquid composition containing water, which satisfies at least one of the following (i) and (ii): (i) after storage at 40° C. for 2 weeks, a residual rate of the compound of formula (1) or a salt thereof in the composition is 90% or more by mass, or (ii) the proportion of the peak area of a decomposition product derived from the compound of formula (1) to the total peak area by HPLC analysis of the composition obtained after storage at 40° C. for 2 weeks is 10% or less by area.

According to another embodiment of the present invention, there is provided a method for stabilizing a liquid composition, the method comprising making coexist a water-soluble additive, the compound of formula (1) or a salt thereof and water in the liquid composition. Here, suitable examples of the stabilization of the liquid composition mentioned above include solubilization (e.g., inhibition of precipitation), inhibition of coloring and the like.

All of the above embodiments of use, the decomposition inhibiting agent, the water-soluble additive for inhibition of decomposition, the method for inhibiting decomposition and the method for stabilization can be performed in accordance with the mentions on the composition and the method of the present invention.

EXAMPLES

The present invention will be more specifically described by way of Examples, Test Examples and Reference Examples, but the technical scope of the present invention is not limited to these examples. Unless otherwise specified, all of percentages and ratios used in the present invention are by mass. Unless otherwise specified, units and measurement methods mentioned herein are in accordance with the Japanese Industrial Standards (JIS).

Substances used in Examples, Test Examples and Reference Examples are as follows:

Compound 1:
N-(2-ethylsulfonylamino-5-trifluoromethyl-3-pyridyl)cyclohexanecarboxamide-monosodium salt-monohydrate
  Kolliphor (registered trademark) HS 15: manufactured by BASF SE
  Kolliphor (registered trademark) P188: manufactured by BASF SE
  Kolliphor (registered trademark) P407: manufactured by BASF SE
  Kolliphor (registered trademark) ELP: manufactured by BASF SE
  Tween 80 HP-LQ-(MH): manufactured by CRODA (hereinafter referred to as Tween 80 HP)
  NIKKOL HCO-60: manufactured by NIPPON SURFACTANT INDUSTRIES CO., LTD.
  Celldex (registered trademark) HP-β-CD: manufactured by NIHON SHOKUHIN KAKO CO., LTD. (hereinafter referred to as HP-β-CD)
  Methyl-β-cyclodextrin: manufactured by JUNSEI CHEMICAL CO., LTD. (hereinafter referred to as M-β-CD)
  2-Hydroxypropyl-α-cyclodextrin: manufactured by Aldrich (hereinafter referred to as HP-α-CD)
  Sulfobutyl ether-β-cyclodextrin: manufactured by NACALAI TESQUE, INC. (hereinafter referred to as SBE-β-CD)
  Phosphate buffer: 0.025 M sodium dihydrogenphosphate solution+0.025 M disodium hydrogenphosphate solution
  Britton-Robinson buffer (hereinafter referred to as BR buffer): 0.04 M acid mixed solution (0.04 M phosphoric acid+0.04 M acetic acid+0.04 M boric acid)+0.2 M NaOH solution
  Vitamin C (L-ascorbic acid): manufactured by NACALAI TESQUE, INC.
  L-Cysteine (also referred to as cysteine in Example 8): manufactured by Aldrich
  Sodium azide ($NaN_3$): manufactured by Wako Pure Chemical Industries, Ltd.
  Sodium sulfite ($Na_2SO_3$): manufactured by Wako Pure Chemical Industries, Ltd.
  Tween 80: manufactured by Wako Pure Chemical Industries, Ltd.

Apparatuses used in Examples, Test Examples and Reference Examples are as follows:
  Magnetic stirrer: PASOLINA Mini Stirrer CT-1AT, AS ONE Corporation
  pH meter: LAQUA F-72, manufactured by HORIBA, Ltd.
  Sterilization filter: DISMIC-25AS, manufactured by ADVANTEC Incubator: PIC-100, manufactured by TAIYO CANPANY CO., LTD Light resistance tester: Atlas Suntest CPS+, manufactured by Atlas Material Technology LCC Measurement of the content of the compound 1 and the decomposition product D1 in the following Example 1 (decomposition inhibition test of the compound 1) was performed using HPLC (high performance liquid chromatography) under the following conditions:

Analyzer: HPLC ACQUITY Arc system, manufactured by Water Corporation

Measurement of the content of the compound 1: absolute calibration method

Measurement of the content of the decomposition product D1: area percentage method Measurement conditions Detector: 2998PDA Detector, manufactured by Water Corporation Column: XBridge C18 5 m (4.6×250 mm), manufactured by Water Corporation Detailed conditions are shown in Table 2.

TABLE 2

| Column temperature | 40° C. |
|---|---|
| Mobile phase | Water/acetonitrile/acetic acid = 42/57.5/0.5 |
| Flow rate | 0.7 mL/min |
| Injection volume | 10 μL |
| Detection | 276 nm |
| Analysis time | 40 min |
| Retention time | Compound 1: 34 to 35 min<br>D1: 7.5 to 8 min |

Example 1: Decomposition Inhibition Test of Compound 1

(a) Preparation of Compound 1-Containing Liquid Composition (Test Examples 1 to 18)

A water-soluble additive was metered into a 50 mL screw cap bottle, and a phosphate buffer or a BR buffer (30 mL) was added, followed by dissolution by mixing with a magnetic stirrer. Water used for the preparation of the phosphate buffer and the BR buffer was distilled water. Furthermore, a compound 1 was metered and dissolved, and as needed, using a 0.2 M hydrochloric acid solution or a 0.1 M sodium hydroxide solution, the pH was adjusted to that mentioned in Table 3. The solution thus obtained was transferred into a 50 mL volumetric flask to make a total volume of 50 mL with the buffer used above, and after uniformly stirring, the solution was passed through a sterilization filter to obtain a compound 1-containing liquid composition with a content shown in Table 3 below.

(b) Stability Test of Compound 1-Containing Liquid Composition (Test Example 1 to 18)

For the compound 1-containing liquid composition produced in (a), the pH (initial) was measured and the appearance (color, solubility) was observed, and then the liquid composition was stored at 40° C. for 2 weeks.

The content of the compound 1 in the liquid composition produced was measured by HPLC, and the value thereof was regarded as the initial content. After storage, the appearance (color, solubility) was confirmed and the pH was measured, and then the residual rate (% by mass) of the compound 1 in the liquid composition and the content of the decomposition product D1 were measured by HPLC. The residual rate (% by mass) of the compound 1 in the liquid composition was calculated by the following mathematical expression (1). The content of D1 was represented by area percentage of HPLC.

$$\text{Residual rate (\% by mass) of compound 1} = (\text{content after 2 weeks/initial content}) \times 100 \quad (1)$$

The results thus obtained are shown in Table 3.

Here, the solubility was confirmed by panels having healthy visual acuity (visual acuity of 0.7 or more) under light with an illuminance of 300 to 2,000 lux. The confirmation was performed by three panels. As a result, no precipitate was observed at the initial stage and after 2 weeks at 40° C. in Test Examples 1 to 18.

As Reference Examples, a decomposition inhibition test was also performed for a compound 1-containing liquid composition containing no water-soluble additive.

(a) Preparation of Compound 1-Containing Liquid Composition (Reference Examples 1 to 3)

A compound 1 was metered into a 50 mL screw cap bottle, and a phosphate buffer or a BR buffer (30 mL) was added, followed by dissolution by mixing with a magnetic stirrer. Furthermore, using a 0.1 M sodium hydroxide solution, the pH was adjusted to that mentioned in Table 3. The total volume of the solution thus obtained was made 50 mL with the buffer used above, and after making uniform by stirring, the solution was passed through a sterilization filter to obtain a compound 1-containing liquid composition with a content shown in Table 3 below.

(b) Stability Test of Compound 1-Containing Liquid Composition (Reference Examples 1 to 3)

A stability test of the compound 1-containing liquid composition produced in (a) was performed in the same manner as in Test Example 1. The results thus obtained are shown in Table 3.

Confirmation of a precipitate was performed in the same manner as in Test Examples 1 to 18. As a result, no precipitate was observed at the initial stage and after 2 weeks at 40° C. in Reference Examples 1 to 3.

TABLE 3

| | | | Test Example 1 | Test Example 2 | Test Example 3 | Test Example 4 | Test Example 5 | Test Example 6 | Test Example 7 |
|---|---|---|---|---|---|---|---|---|---|
| Content (w/v %) of compound 1 | | | 0.04 | 0.04 | 0.04 | 0.4 | 0.04 | 0.04 | 0.4 |
| Water-soluble additive | Component | | Kolliphor HS15 | Kolliphor HS15 | Kolliphor HS15 | Kolliphor HS15 | Kolliphor HS15 | Kolliphor P188 | Kolliphor P188 |
| | Content (w/v %) | | 10 | 10 | 5 | 5 | 10 | 5 | 5 |

TABLE 3-continued

| Buffer used (1; phosphate, 2; BR) | | 2 | 2 | 1 | 1 | 2 | 1 | 1 |
|---|---|---|---|---|---|---|---|---|
| Appearance (color, solubility) | Initial | Bluish clear | Bluish clear | Clear and colorless | Clear and colorless | Clear and colorless | Clear and colorless | Clear and colorless |
| | After 2 weeks at 40° C. | Bluish clear | Bluish clear | Clear and colorless | Clear and colorless | Clear and colorless | Clear and colorless | Clear and colorless |
| pH | Initial | 5.0 | 6.0 | 7.0 | 8.0 | 9.0 | 7.0 | 8.0 |
| | After 2 weeks at 40° C. | 5.0 | 6.0 | 7.0 | 7.7 | 8.7 | 7.0 | 7.6 |
| Residual rate (% by mass) of compound 1 After 2 weeks at 40° C. | | 99.5 | 98.7 | >99.9 | 94.8 | 98.8 | 94.7 | 92.6 |
| Content (% by area) of decomposition product D1 After 2 weeks at 40° C. | | <0.1 | 0.2 | 0.7 | 3.2 | 0.3 | 5.6 | 5.2 |

| | | Test Example 8 | Test Example 9 | Test Example 10 | Test Example 11 | Test Example 12 | Test Example 13 | Test Example 14 |
|---|---|---|---|---|---|---|---|---|
| Content (w/v %) of compound 1 | | 0.04 | 0.04 | 0.04 | 0.04 | 0.04 | 0.04 | 0.4 |
| Water-soluble additive | Component | Kolliphor P188 | Kolliphor ELP | Tween 80HP | Nikkol HCO-60 | HP-β-CD | HP-β-CD | HP-β-CD |
| | Content (w/v %) | 10 | 5 | 5 | 5 | 10 | 10 | 10 |
| Buffer used (1; phosphate, 2; BR) | | 2 | 1 | 1 | 1 | 2 | 2 | 1 |
| Appearance (color, solubility) | Initial | Clear and colorless | Clear and colorless | Clear and colorless | Clear and colorless | Clear and colorless | Clear and colorless | Clear and colorless |
| | After 2 weeks at 40° C. | Clear and colorless | Clear and colorless | Clear and colorless | Clear and colorless | Clear and colorless | Clear and colorless | Clear and colorless |
| pH | Initial | 9.0 | 7.0 | 7.0 | 7.0 | 5.0 | 6.0 | 7.0 |
| | After 2 weeks at 40° C. | 8.9 | 7.0 | 6.8 | 7.0 | 5.0 | 6.0 | 6.9 |
| Residual rate (% by mass) of compound 1 After 2 weeks at 40° C. | | 97.6 | 99.3 | 99.8 | 99.4 | 97.2 | 93.4 | 94.5 |
| Content (% by area) of decomposition product D1 After 2 weeks at 40° C. | | 1.5 | 0.6 | 0.5 | 0.8 | 2.1 | 4.1 | 2.8 |

| | | Test Example 15 | Test Example 16 | Test Example 17 | Test Example 18 | Reference Example 1 | Reference Example 2 | Reference Example 3 |
|---|---|---|---|---|---|---|---|---|
| Content (w/v %) of compound 1 | | 0.04 | 0.4 | 0.4 | 0.4 | 0.04 | 0.4 | 0.04 |
| Water-soluble additive | Component | HP-β-CD | M-β-CD | HP-α-CD | SBE-β-CD | None | None | None |
| | Content (w/v %) | 10 | 10 | 10 | 8 | — | — | — |
| Buffer used (1; phosphate, 2; BR) | | 2 | 1 | 1 | 1 | 1 | 1 | 2 |
| Appearance (color, solubility) | Initial | Clear and colorless | Clear and colorless | Clear and colorless | Clear and colorless | Clear and colorless | Clear and colorless | Clear and colorless |
| | After 2 weeks at 40° C. | Clear and colorless | Clear and colorless | Clear and colorless | Clear and colorless | Clear and colorless | Clear and colorless | Clear and colorless |
| pH | Initial | 9.0 | 7.0 | 7.0 | 7.0 | 7.2 | 8.0 | 8.0 |
| | After 2 weeks at 40° C. | 9.0 | 6.9 | 6.9 | 6.9 | 7.2 | 7.3 | 7.9 |
| Residual rate (% by mass) of compound 1 After 2 weeks at 40° C. | | 92.6 | 96.5 | 97.8 | 97.4 | 86.8 | 87.5 | 84.8 |
| Content (% by area) of decomposition product D1 After 2 weeks at 40° C. | | 3.3 | 4.0 | 1.6 | 3.9 | 12.7 | 12.5 | 13.0 |

Example 2: Preparation of Compound 1-Containing Liquid Composition

A nonionic surfactant (10 g) is metered into a 100 mL glass beaker, followed by heating to 60° C., and then a compound 1 (0.42 g) is metered and added, followed by dissolution by mixing with a magnetic stirrer. To this, a phosphate buffer (70 mL) which was heated to 60° C. and the pH was adjusted to 7.0 is added, followed by dissolution by mixing. The solution is allowed to cool to room temperature, and as needed, using a 0.2 M hydrochloric acid solution or a 0.1 M sodium hydroxide solution, the pH is adjusted to 7.0. The solution thus obtained is transferred into a 100 mL volumetric flask to make a total volume of 100 mL with a phosphate buffer at room temperature and with the pH being adjusted to 7.0, and after uniformly stirring, the solution is passed through a sterilization filter to obtain a compound 1-containing liquid composition.

Examples 3 to 8: Forced Decomposition Test of Compound 1

The production mechanism of the decomposition products D1 and D3 that are produced when the compound 1 is decomposed has not been clear. A forced decomposition test of the compound 1 was performed to elucidate these production factors, and design of formulation directed toward inhibition of decomposition was attempted.

A forced decomposition test of the compound 1 was performed under stress conditions of heat, acid, base, oxidation and light. A compound 1-containing solution was stored under the conditions shown in Table 4 below, and then the concentrations of the compound 1 and the decomposition products in the solution were measured using a high performance liquid chromatography-photodiode array detector (HPLC-PDA system). An incubator was used for heating, and a light resistance tester was used for irradiation with pseudo-sunlight in a photodecomposition test. The content of the compound 1 in the compound 1-containing solution produced was measured by the HPLC-PDA system, and the value thereof was regarded as the initial content.

The content of D1 and D3 in the solution was represented by the proportion (% by area) of the peak area of each compound to the total peak area of HPLC analysis of the composition obtained after the decomposition test. Furthermore, the residual rate (% by mass) of the compound 1 was calculated by dividing the content after storage by the initial content using the absolute calibration method.

TABLE 4

Forced decomposition test of compound 1

| | Condition | Time (h) |
|---|---|---|
| Heat | 60° C. | 48 |
| Acid | 0.1 HCl (60° C.) | 48 |
| Base | 0.1 NaOH (60° C.) | 48 |
| Oxidation | 3.0% $H_2O_2$ (room temperature) | 48 |
| Light | 250 W/m² (room temperature) | 2 |

Measurement of the residual rate of the compound 1 and the content of the decomposition products in the following Examples 3 to 9 was performed under the following conditions:

Analyzer: HPLC-PDA system: CBM-20Avp system controller, SIC-20ADvp autosampler, LC-20ADvp feed pump, DGU-20A degasser, CTO-20Avp column oven, SPD-M10Avp photodiode array detector, manufactured by Shimadzu Corporation Column: Kinetex® Biphenyl 2.6 m (50×4.6 mm), manufactured by Shimadzu Corporation Detailed conditions are shown in Table 5.

TABLE 5

| Column temperature | 40° C. | | |
|---|---|---|---|
| Mobile phase | Solution A: Milli-Q water containing 0.1% formic acid | | |
| | Solution B: Methanol containing 0.1% formic acid | | |
| | Performed with the following gradient program | | |
| | Time (min) | % of solution A | % of solution B |
| | At the time of start | 65 | 35 |
| | 2.0 | 65 | 35 |
| | 15.0 | 5 | 95 |

TABLE 5-continued

| Flow rate | 0.3 mL/min |
|---|---|
| Injection volume | 10 μL |
| Detection | 276 nm |
| Retention time | Compound 1: about 13.1 min |
| | D1: about 10.8 min |
| | D3: about 2.4 min |

Example 3: Forced Decomposition Test (Thermal Decomposition) of Compound 1

A compound 1 was metered, and Milli-Q water was added so that the compound 1 could be solubilized, thus obtaining an aqueous solution of the compound 1 (250 μM) so that the concentration of the compound 1 became 250 μM.

The aqueous solution of the compound 1 thus obtained (250 μM) was heated at 60° C., followed by measurement using the HPLC-PDA system. The results are shown in FIG. 1. The residual rate of the compound 1 was 88.7% by mass, the content of D1 was 8.08% by area, and D3 was below the detection limit. No other peaks were detected.

Example 4: Forced Decomposition Test (Acid Decomposition) of Compound 1

Figure 2:
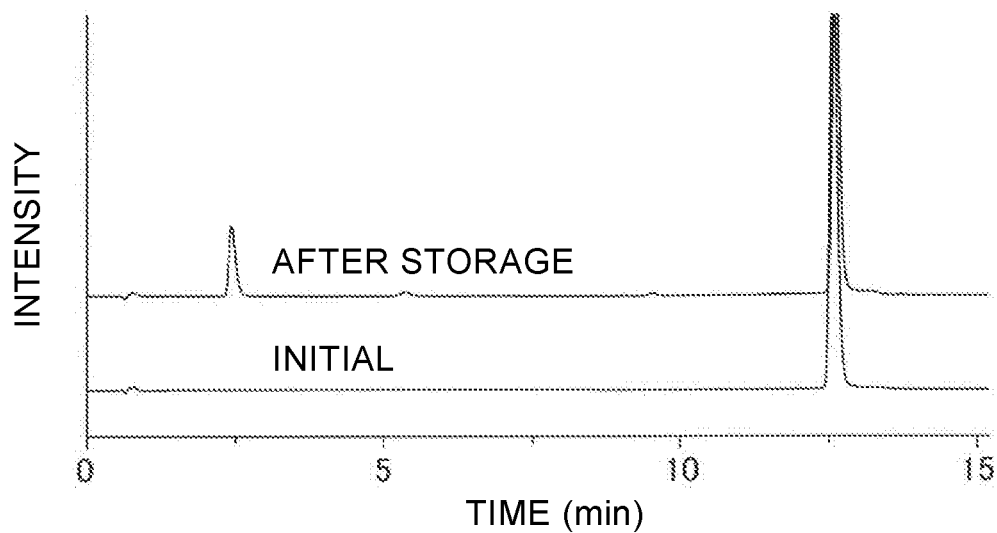
FIG. 2 is an HPLC chromatogram of the aqueous solution of the compound 1 before and after acid decomposition.

The aqueous solution of the compound 1 obtained in Example 3 (250 μM) was heated under acid (0.1N HCl) conditions, followed by measurement of the decomposition products using the HPLC-PDA system. The results are shown in FIG. 2. The residual rate of the compound 1 was 77.1% by mass, the content of D3 was 16.18% by area, and D1 was below the detection limit. Addition of an acid decreased the production of D1 and promoted the production of D3. Other peaks were slightly (a maximum of 1.36% by area) observed.

Example 5: Forced Decomposition Test (Base Decomposition) of Compound 1

Figure 3:
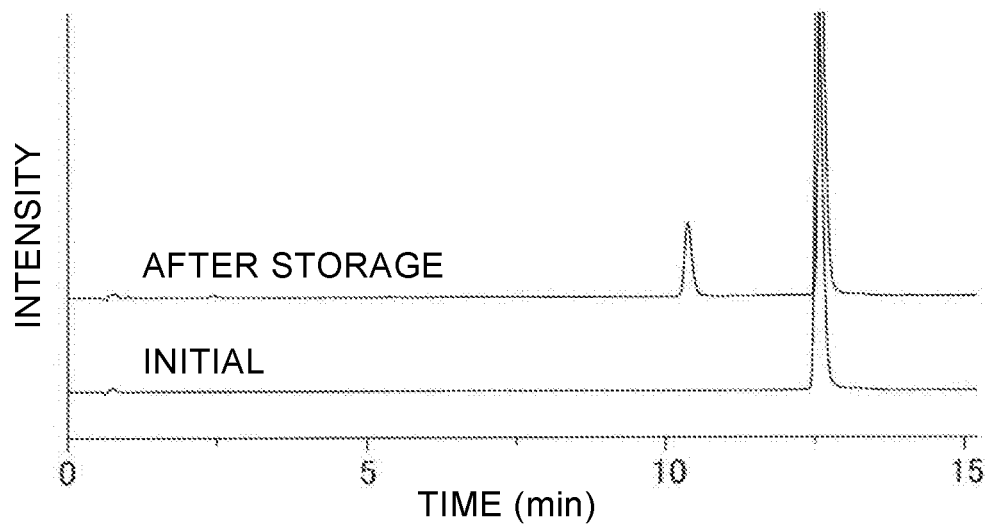
FIG. 3 is an HPLC chromatogram of the aqueous solution of the compound 1 before and after base decomposition.

The aqueous solution of the compound 1 obtained in Example 3 (250 μM) was heated under base (0.1N NaOH) conditions, followed by measurement of the decomposition products using the HPLC-PDA system. The results are shown in FIG. 3. The residual rate of the compound 1 was 77.3% by mass, the content of D1 was 17.62% by area, and the content of D3 was 0.50% by area. Addition of a base promoted the production of D1. Other peaks (0.11% by area) were observed.

Example 6: Forced Decomposition Test (Oxidative Decomposition) of Compound 1

Figure 4:
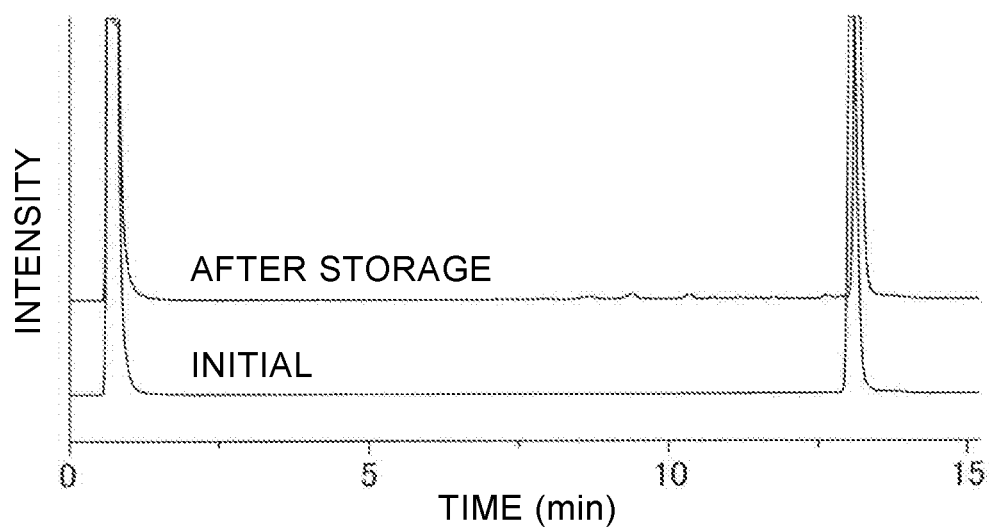
FIG. 4 is an HPLC chromatogram of the aqueous solution of the compound 1 before and after oxidative decomposition.

The aqueous solution of the compound 1 obtained in Example 3 (250 μM) was stored under conditions of ordinary temperature and hydrogen peroxide (3 v/v %), followed by measurement of the decomposition products using the HPLC-PDA system. The results are shown in FIG. 4. The residual rate of the compound 1 was 75.9% by mass, the content of D1 was 0.30% by area, and D3 was below the detection limit. Many peaks other than the peaks of D1 and D3 were observed (a maximum of 1.79% by area).

Example 7: Forced Decomposition Test (Photodecomposition) of Compound 1

Figure 5:
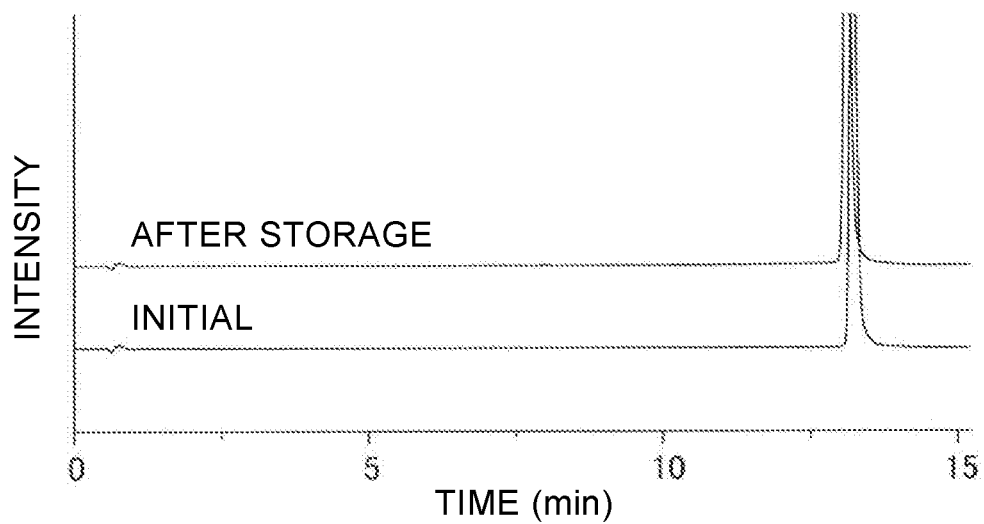
FIG. 5 is an HPLC chromatogram of the aqueous solution of the compound 1 before and after photodecomposition.

The aqueous solution of the compound 1 obtained in Example 3 (250 μM) was irradiated with pseudo-sunlight (250 W/m², 2 hours), followed by measurement of the decomposition products using the HPLC-PDA system. The results are shown in FIG. 5. No decomposition product was detected. Therefore, it was confirmed that the aqueous solution of the compound 1 was photostable.

Table 6 and Table 7 show the results of the forced decomposition test. Of the main decomposition products, D1 remarkably increased even under the conditions of only heating, and it is considered that the production of D1 is greatly involved in the stability of the compound 1 in a solution state.

TABLE 6

% by area of decomposition products derived from the compound 1 after the forced decomposition test

| Peak | Relative retention time (that of compound 1 is regarded as 1) | % by area of compound 1 and decomposition products thereof | | | |
|---|---|---|---|---|---|
| | | Heat | Acid | Base | Oxidation | Light |
| D3 | 0.19 | — | 16.18 | 0.50 | — | — |
| D1 | 0.83 | 8.08 | — | 17.62 | 0.30 | — |

—: Undetected

TABLE 7

Residual rate (% by mass) of the compound 1 after the forced decomposition test

| | % by mass Compound 1 |
|---|---|
| Heat | 88.7 |
| Acid | 77.1 |
| Base | 77.3 |
| Oxidation | 75.9 |
| Light | 97.4 |

Figure 6:
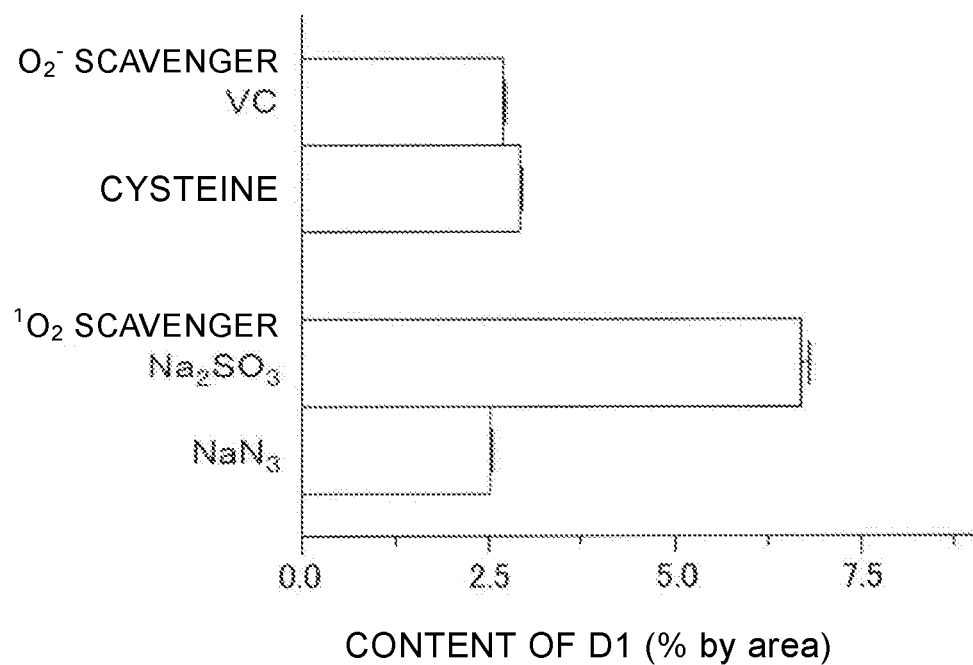
FIG. 6 is a graph showing the content of D1 (compound of formula (2)) after the compound 1-containing liquid composition was stored under heating in the presence of an antioxidant. As the antioxidant, vitamin C (hereinafter also referred to as VC) or cysteine was used as an $O_2^-$ scavenger, and sodium azide ($NaN_3$) or sodium sulfite ($Na_2SO_3$) was used as an $^1O_2$ scavenger. Data represent values of mean±standard error (n=3).

Example 8: Investigation of Inhibition of Decomposition of Compound 1-Containing Liquid Composition with Antioxidant Added In this test, an additive (antioxidant) that traps reactive oxygen species (ROS) was added to investigate the usefulness in the aqueous solution of the compound 1 for inhibition of decomposition under thermal conditions. A compound 1, Tween 80 and an antioxidant was metered, and Milli-Q water was added so that the concentration of the compound 1 and Tween 80 became 250 μM and 1.0 v/v %, respectively. Subsequently, four antioxidants were added so that each of the concentration thereof became 250 μM to obtain a compound 1-containing liquid composition with an antioxidant added. The content of D1 after the composition was heated at 60° C. for 48 hours was evaluated. The results are shown in FIG. 6. As the antioxidant, vitamin C (hereinafter also referred to as VC) and cysteine, which are $O_2^-$ scavengers, and sodium azide ($NaN_3$) and sodium sulfite ($Na_2SO_3$), which are $^1O_2$ scavengers, were selected. Addition of an additive inhibited the decomposition of the compound 1, and particularly addition of VC, cysteine and $NaN_3$ remarkably inhibited the production of D1. The maximum dose during intravenous injection of VC and cysteine is 2,800 mg and 8 mg, respectively, and VC can be administered at a 350-fold higher dose and is clinically safe.

Figure 7:
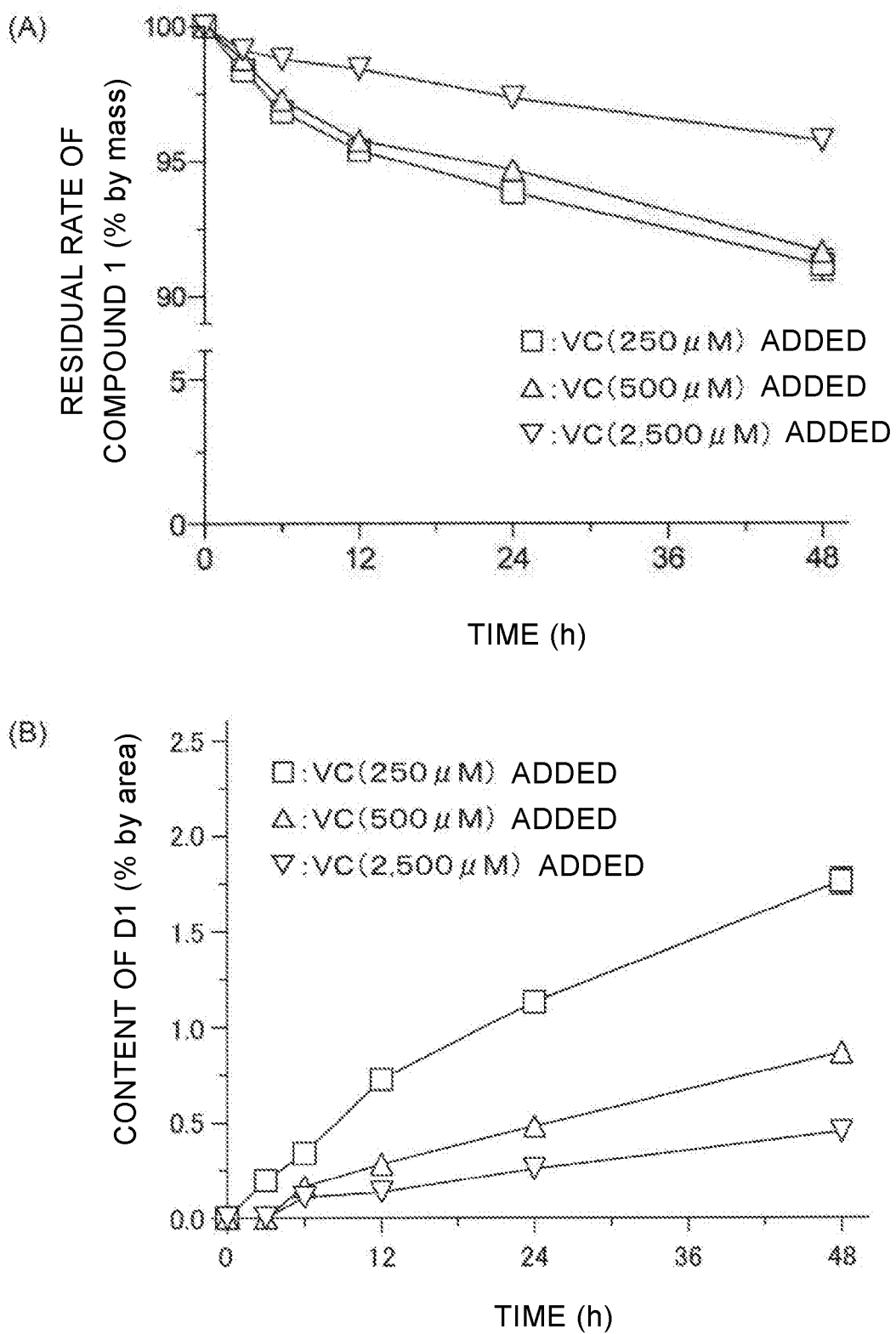
FIG. 7(A) is a graph showing changes in the residual rate of the compound 1 in the compound 1-containing liquid composition stored under heating after addition of VC at various concentrations (250, 500 and 2,500 μM).
FIG. 7(B) is a graph showing changes in the content of D1 in the compound 1-containing liquid composition stored under heating after addition of VC at various concentrations (250, 500 and 2,500 μM).

Example 9: Evaluation of Solution Stability of Compound 1-Containing Liquid Composition with VC Added Effects of the amount of VC added on the solution stability of the compound 1 were investigated. Preparation was performed in the same manner as for the compound 1-containing liquid composition in Example 8 except that the concentration of VC was 250, 500 or 2,500 μM. The decomposition of the compound 1 and the production of D1 at the time of addition were evaluated (mean±standard error, n=3). After heating to 60° C., and the residual rate of the compound 1 and the content of D1 were evaluated over time, and the results are shown in FIG. 7. The residual rate (% by mass) of the compound 1 in the solution and the content (% by area) of D1 were calculated by the same calculation method as in Examples 3 to 8. As a result, the residual rate of the compound 1 increased depending on the concentration of VC added, and the content of D1 decreased depending on the concentration of VC added, confirming that addition of VC is useful for improving the stability of the compound 1 in a solution state.

Example 10: Pharmacokinetic Evaluation of Compound 1-Containing Liquid Composition with VC Added In order to investigate the effects of addition of VC on the disposition of the compound 1, a compound 1-containing liquid composition obtained by adding an excessive amount of VC (2.2 mg/kg, 10-fold amount based on molar ratio to the compound 1) to the compound 1 (0.5 mg/kg) and a compound 1-containing liquid composition without VC addition were intravenously injected to rats to analyze the disposition of the compound 1.

As an animal experiment, 9 to 10-week-old Sprague-Dawley (SD) male rats were purchased from Japan SLC, Inc. This test was performed by dividing into two groups (n=6) of the compound 1 alone administration group and the compound 1 and VC co-administration group. In the compound 1 alone administration group, the compound 1 and Tween 80 were dissolved in physiological saline so that the concentration thereof became 250 μM and 1 v/v %, respectively, to prepare a compound 1-containing liquid composition. In the compound 1 and VC co-administration group, the compound 1, VC and Tween 80 were dissolved in physiological saline so that the concentration thereof became 250 μM, 2,500 μM and 1 v/v %, respectively, to prepare a compound 1- and VC-containing liquid composition. In the compound 1 and VC co-administration group, each of the compound 1— and VC—(compound 1-0.5 mg/kg, VC-2.2 mg/kg) containing liquid compositions was administered into the tail vein of rats (n=6) fasted from 24 hours before administration using a 23G injection needle and a 1 mL syringe. In the compound 1 alone administration group, each of the compound 1—(compound 1-0.5 mg/kg) containing liquid compositions was administered into the tail vein of rats fasted from 24 hours before administration using a 23G injection needle and a 1 mL syringe. Blood samples (about 400 μL) were collected from the tail vein of the rats immediately after administration of the compound 1-containing liquid composition or the compound 1- and VC-containing liquid composition into the tail vein and at 5, 15, 30, 60, 180, 360 and 720 minutes after administration, and then the samples were centrifuged at 10,000×g and 4° C. for 10 minutes to obtain plasma. The concentration of the compound 1 was measured by ultra-high performance liquid chromatography-electrospray ionization-mass spectrometry (UPLC/ESI-MS) under the conditions mentioned in Table 8.

Analyzer: ACQUITY UPLC, manufactured by Water Corporation

Detector: ACQUITY SQD, manufactured by Water Corporation

TABLE 8

| Column | Aquity UPLC BEC C18 Column (manufactured by Water Corporation) |
|---|---|
| Column temperature | 40° C. |
| Mobile phase | Solution A: Milli-Q water containing 0.1% formic acid<br>Solution B: Methanol containing 0.1% formic acid<br>Performed with the following gradient program |

| Time (min) | % of solution A | % of solution B |
|---|---|---|
| At the time of start | 40 | 60 |
| 0.50 | 40 | 60 |
| 3.50 | 20 | 80 |

| Flow rate | 0.25 mL/min |
|---|---|
| Injection volume | 5 μL |
| Detection | Mass spectrometer<br>ESI negative<br>Selected ion monitoring<br>(m/z of compound 1: 378.1) |
| Retention time | About 2.6 min (compound 1) |

Figure 8:
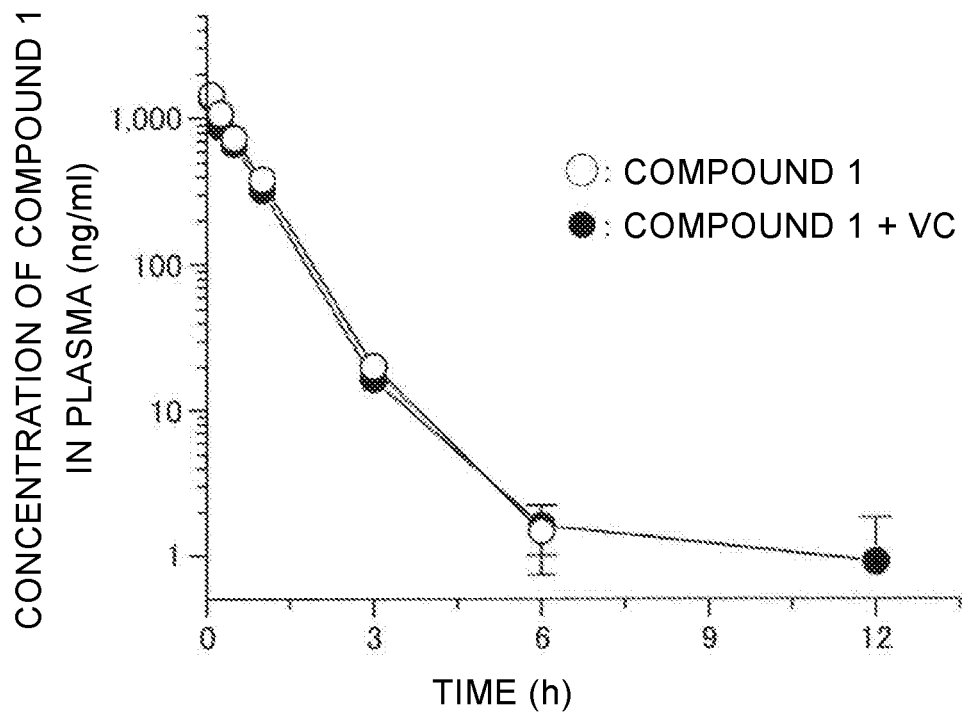
FIG. 8 is a graph showing concentration changes of the compound 1 in plasma of rats in the compound 1 alone administration group and the compound 1 and VC co-administration group. Data represent values of mean±standard error (n=6).

Comparison of changes in the blood concentration of the compound 1 in both groups showed almost similar changes in the blood concentration (FIG. 8). For detailed analysis based on the pharmacokinetic parameters, $k_e$ and $AUC_{0-inf}$ were calculated by non-compartment model analysis (Table 9). The elimination velocity constant ($k_e$) and the area under the blood concentration-time curve ($AUC_{0-inf}$) of the compound 1 alone administration group were 1.43 h$^{-1}$ and 1,271 ng·h/mL, respectively. On the other hand, $k_e$ and $AUC_{0-inf}$ of the compound 1/VC co-administration group were 1.54 h$^{-1}$ and 1,122 ng·h/mL, respectively. $k_e$ and $AUC_{0-inf}$ of both groups were statistically treated by the Fisher's least significant difference procedure, and no significant difference was observed (P>0.05), confirming that addition of VC does not affect the pharmacokinetics of the compound 1.

TABLE 9

| | $k_e$(h$^{-1}$) | $AUC_{0-inf}$(ng · h/mL) |
|---|---|---|
| Compound 1 | 1.43 ± 176 | 1,271 ± 176 |
| Compound 1 + VC | 1.54 ± 0.25 | 1,122 ± 220 |

In Table 9, each pharmacokinetic parameter was expressed as mean±standard error (n=6).

Example 11: Investigation of Compound 1-Containing Liquid Composition (Hydrogelated Liquid Composition)

(a) Preparation of Compound 1-Containing Liquid Composition (Hydrogelated Liquid Composition)

A compound 1 (3.5 mg), Kolliphor (registered trademark) P188 (200 mg), Kolliphor (registered trademark) P407 (150 mg) and purified water (1.0 mL) were mixed using a vortex mixer to obtain a liquid composition. Then, the above liquid composition was stored at 4° C. overnight to obtain a hydrogel.

(b): Pharmacokinetic Evaluation of Compound 1-Containing Liquid Composition (Hydrogelated Liquid Composition)

Figure 9:
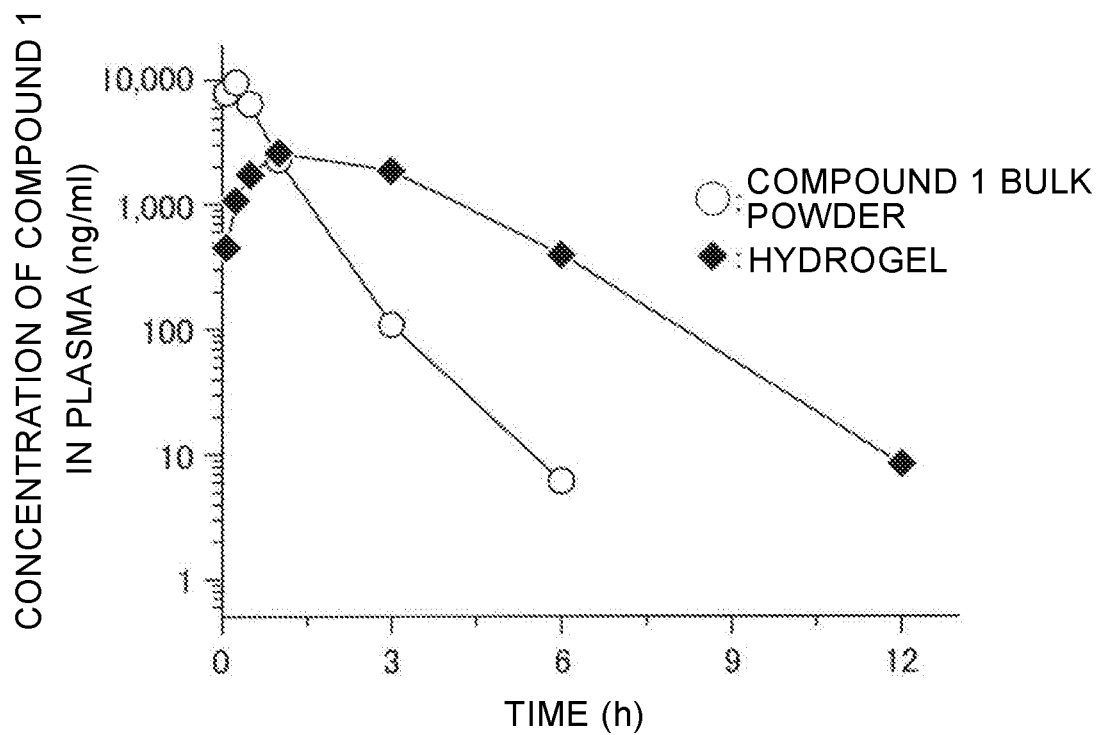
FIG. 9 is a graph showing concentration changes of the compound 1 in plasma of rats in the compound 1 bulk powder administration group and the compound 1-containing liquid composition (hydrogelated liquid composition) administration group. Data represent values of mean±standard error (n=3 to 6).

To evaluate the sustained-release ability of the hydrogelated liquid composition prepared in the above Example 11(a), the drug concentration in blood was measured over time after subcutaneous administration of the hydrogel or a compound 1 bulk powder to rats. Specifically, the hydrogel or the compound 1 bulk powder, at a dose of 5 mg/kg as an amount of the compound 1, was singly subcutaneously administered to SD male rats. After subcutaneous administration, blood was collected over time from the tail vein, and the blood was transferred into a micro test tube treated with heparin, and immediately cooled in ice. After cooling in ice, the blood was immediately centrifuged at 4° C. and 10,000 g for 10 minutes. The concentration of the compound 1 in plasma thus obtained was quantitatively determined by ultra-high performance liquid chromatography-electrospray ionization-mass spectrometry in the same manner as in Example 10. The results are shown in FIG. 9. The following Table 10 shows the pharmacokinetic parameters calculated from the results of blood drug concentration measurement.

TABLE 10

| | $C_{max}$ (μ/mL) | $T_{max}$ (h) | $T_{1/2}$ (h) |
|---|---|---|---|
| Compound 1 bulk powder | 9.6 ± 0.7 | 0.25 ± 0.0 | 0.36 ± 0.0 |
| Hydrogel | 2.6 ± 0.1 | 1.0 ± 0.0 | 1.8 ± 0.6 |

In Table 10, pharmacokinetic parameter was expressed as mean±standard error (n=3 to 6).

From the results of the above Table 10 and FIG. 9, the compound 1-containing liquid composition (hydrogelated liquid composition) had decreased absorption and elimination velocity of the compound 1, compared with the compound 1 bulk powder. Here, the $C_{max}$ of the hydrogel was decreased by 73% compared with that of the compound 1 bulk powder. The $T_{1/2}$ of the hydrogel was prolonged by 1.44 hours compared with that of the compound 1 bulk powder, and the hydrogel of Example 11 showed increased retention in blood of the compound 1. At 12 hours after administration, the concentration of the compound 1 bulk powder in plasma was below the detection limit, while the concentration of the hydrogel in plasma was 8 ng/mL. This is estimated to be due to the fact that the hydrogel prepared in Example 11(a) has a sustained-release drug elution property.

The invention claimed is:
1. A liquid composition comprising
a compound of formula (1) or a salt thereof:

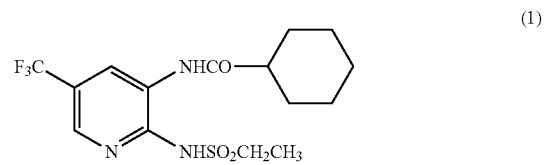

(1)

a water-soluble additive, and
water,
wherein the water-soluble additive is at least one selected from the group consisting of polyoxyethylene hydroxy fatty acid ester, poloxamer, polyoxyethylene castor oil, polyoxyethylene hardened castor oil, hydroxypropyl-β-cyclodextrin, methyl-β-cyclodextrin, hydroxypropyl-α-cyclodextrin, sulfobutyl ether-β-cyclodextrin, cysteine, sodium sulfite and sodium azide, wherein, after storage at 40° C. for 2 weeks, a residual rate of the compound of formula (1) or a salt thereof in the composition is 90% or more by mass, wherein the content of the compound of formula (1) or a salt thereof in the composition is 0.01 to 1 w/v %, and wherein a mass ratio of the compound of formula (1) or a salt thereof to the water-soluble additive [compound of formula (1) or salt thereof:water-soluble additive] is 1:0.02 to 1:1,300.

2. The composition according to claim 1, wherein the pH is 4 to 10.

3. The composition according to claim 1, wherein the composition is an aqueous solution, and the aqueous solution does not contain a precipitate after storage at 40° C. for 2 weeks.

4. A product comprising the composition according to claim 1 filled in a vial or a syringe.

5. The composition according to claim 1, wherein a decomposition product from the compound of formula (1) or a salt thereof is at least one selected from compounds of formulas (2) to (4):

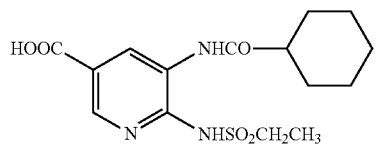

(2)

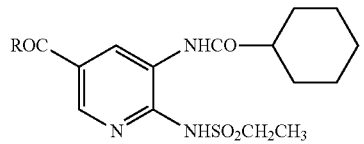

(3)

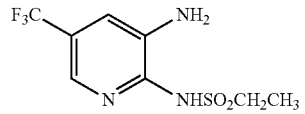

(4)

wherein R is an optionally substituted amino group or an optionally substituted alkoxy group.

6. A method for inhibiting decomposition of the compound of formula (1) or a salt thereof according to claim 1, the method comprising making a water-soluble additive and the compound of formula (1) or a salt thereof coexist in a liquid composition containing water, wherein the water-soluble additive is at least one selected from the group consisting of polyoxyethylene hydroxy fatty acid ester, poloxamer, polyoxyethylene castor oil, polyoxyethylene hardened castor oil, hydroxypropyl-β-cyclodextrin, methyl-β-cyclodextrin, hydroxypropyl-α-cyclodextrin, sulfobutyl ether-β-cyclodextrin, cysteine, sodium sulfite and sodium azide, wherein the content of the compound of formula (1) or a salt thereof in the composition is 0.01 to 1 w/v %, and wherein a mass ratio of the compound of formula (1) or a salt thereof to the water-soluble additive [compound of formula (1) or salt thereof:water-soluble additive] is 1:0.02 to 1:1,300.

7. A method for stabilizing a liquid composition, the method comprising making coexist a water-soluble additive, the compound of formula (1) or a salt thereof according to claim 1 and water in the liquid composition, wherein the water-soluble additive is at least one selected from the group consisting of polyoxyethylene hydroxy fatty acid ester, poloxamer, polyoxyethylene castor oil, polyoxyethylene hardened castor oil, hydroxypropyl-β-cyclodextrin, methyl-β-cyclodextrin, hydroxypropyl-α-cyclodextrin, sulfobutyl ether-β-cyclodextrin, cysteine, sodium sulfite and sodium azide, wherein the content of the compound of formula (1) or a salt thereof in the composition is 0.01 to 1 w/v %, and wherein a mass ratio of the compound of formula (1) or a salt thereof to the water-soluble additive [compound of formula (1) or salt thereof:water-soluble additive] is 1:0.02 to 1:1,300.

* * * * *